United States Patent
Nakatomi et al.

(10) Patent No.: US 8,137,286 B2
(45) Date of Patent: Mar. 20, 2012

(54) MONITORING ELECTRODE FOR MONITORING DORSAL COCHLEAR NUCLEUS ACTION POTENTIALS AND MONITORING DEVICE FOR MONITORING DORSAL COCHLEAR NUCLEUS ACTION POTENTIALS

(76) Inventors: Hirofumi Nakatomi, Tokyo (JP); Hidemi Miyazaki, Tokyo (JP)

( * ) Notice: Subject to any disclaimer, the term of this patent is extended or adjusted under 35 U.S.C. 154(b) by 307 days.

(21) Appl. No.: 12/382,288

(22) Filed: Mar. 12, 2009

(65) Prior Publication Data
US 2009/0234421 A1   Sep. 17, 2009

(30) Foreign Application Priority Data
Mar. 12, 2008   (JP) ................. 2008-062138

(51) Int. Cl.
*A61B 5/04*   (2006.01)
*A61N 1/00*   (2006.01)
(52) U.S. Cl. .......................... 600/559; 607/57
(58) Field of Classification Search ........... 607/116–118
See application file for complete search history.

(56) References Cited

U.S. PATENT DOCUMENTS

| | | | |
|---|---|---|---|
| 6,549,814 B1 | 4/2003 | Strutz et al. | |
| 6,556,861 B1 * | 4/2003 | Prichep | 600/544 |
| 7,697,995 B2 * | 4/2010 | Cross et al. | 607/117 |
| 7,797,052 B2 * | 9/2010 | Chiang | 607/76 |
| 2004/0121619 A1 | 6/2004 | Yokoi et al. | |
| 2007/0150039 A1 | 6/2007 | Leigh et al. | |

FOREIGN PATENT DOCUMENTS

| | | |
|---|---|---|
| JP | S63-143305 U | 9/1988 |
| WO | WO 03/035168 A1 | 5/2003 |
| WO | WO 2008/011721 A1 | 1/2008 |

OTHER PUBLICATIONS

European Search Report 09250687.2-2305 dated Jul. 28, 2009.

* cited by examiner

*Primary Examiner* — Carl H Layno
*Assistant Examiner* — Elizabeth K So
(74) *Attorney, Agent, or Firm* — Squire Sanders (US) LLP (57) ABSTRACT

A novel monitoring electrode for monitoring dorsal cochlear nucleus action potentials is provided, which has a superior performance in accuracy, adherent property, comprehensiveness, recording sensitivity, and recording specificity. The monitoring electrode is easily inserted through a foramen of Luschka, stably held on a region of the dorsal cochlear nucleus, and clearly records the dorsal cochlear nucleus action potentials. Additionally, a novel monitoring device for monitoring the dorsal cochlear nucleus action potentials using the monitoring electrode thereof is provided.

5 Claims, 12 Drawing Sheets

FIG.3B midline

MONITORING ELECTRODE FOR MONITORING DORSAL COCHLEAR NUCLEUS ACTION POTENTIALS AND MONITORING DEVICE FOR MONITORING DORSAL COCHLEAR NUCLEUS ACTION POTENTIALS

BACKGROUND OF THE INVENTION

1. Field of the Invention

The present invention relates to a monitoring electrode for monitoring dorsal cochlear nucleus action potentials (DNAPs), and a monitoring device for monitoring the DNAPs using the monitoring electrode for monitoring the DNAPs.

2. Description of the Related Art

Figure 6:
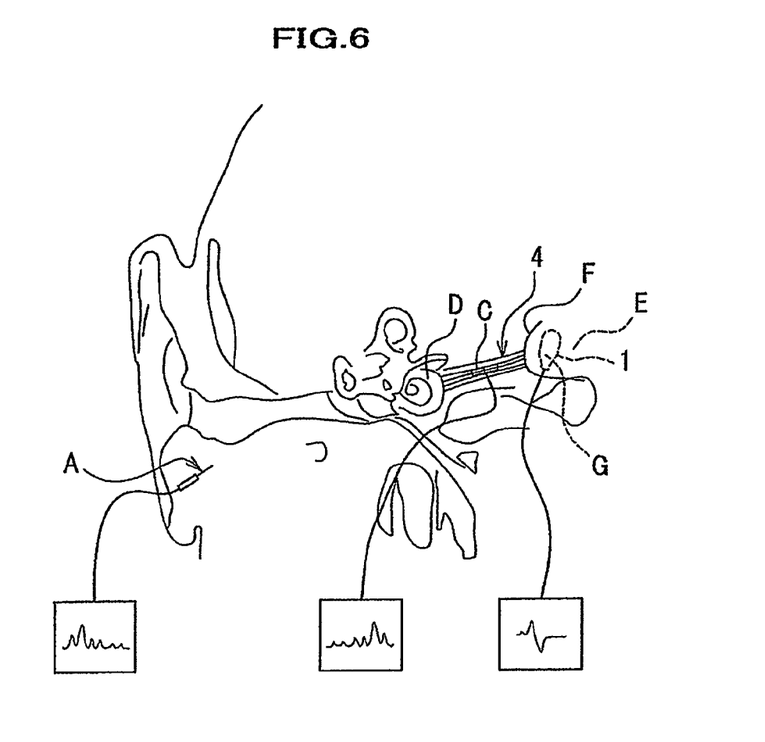
FIG. 6 is a half cross sectional view of a head for explaining a structure of an ear.

FIG. 6 is a half cross sectional diagram of a head explaining a structure of a right ear. As shown in FIG. 6, a human ear comprises an auricle which is a shell-shaped protrusion surrounding an external acoustic meatus located at both sides of the head, an external auditory meatus, an eardrum, an ear ossicle of a middle ear, a cochlea D of an inner ear, and the other organ connecting to an auditory nerve 4. Further, a dorsal cochlear nucleus G is located at a position covered by a cerebellum F, at a brainstem E in the center of the brain.

Figure 7A:
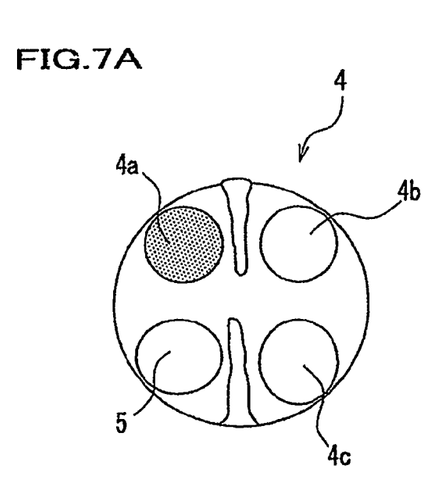
FIG. 7A is a magnified cross sectional view showing an early stage of the acoustic neuroma.
Figure 7B:
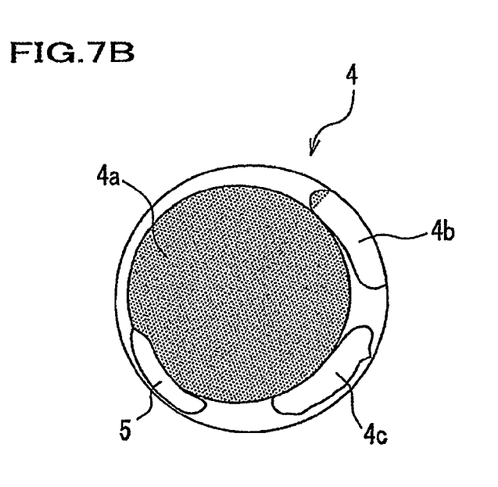
FIG. 7B is a magnified cross sectional view typically showing a late stage of the acoustic neuroma.

FIGS. 7A and 7B are magnified cross sectional views showing a position of nerves in a right internal auditory canal. FIG. 7A is a magnified cross sectional view showing an early stage of an acoustic neuroma. FIG. 7B is a magnified cross sectional view typically showing a late stage of the acoustic neuroma. As shown in FIG. 7A, an auditory nerve 4 includes three types of nerves: a superior vestibular nerve 4a conducting a balance sense, an inferior vestibular nerve 4b, and a cochlear nerve 4c conveying an auditory sense. Adding a facial nerve 5 controlling facial movement, four nerves run in the internal auditory canal.

The acoustic neuroma is a benign tumor, which is frequently found and diagnosed in the field of otolaryngology and neurological surgery by a sign of a deterioration of hearing for an ear at one side. As shown in FIG. 7B, the acoustic neuroma occurs at the superior vestibular nerve 4a or the inferior vestibular nerve 4b, and gradually proliferates toward the brainstem. FIG. 7B is a diagram showing a state that the acoustic neuroma occurs at the superior vestibular nerve 4a. Inside the internal auditory canal, the superior vestibular nerve 4a is located closely adjacent to a facial nerve 5. When the acoustic neuroma is growing, the inferior vestibular nerve 4b is deformed pressed by the acoustic neuroma. As a result, a patient feels a trembling sense and a disorder of a balance sense. Further, symptoms such as a deterioration of hearing caused by the cochlear nerve 4b under pressure, a ringing in ears, and a paralysis of the facial nerve 5, are liable to be shown.

Moreover, if the acoustic neuroma hypertrophies, a trigeminal nerve and the brainstem are pressed to cause a headache and a failing of eyesight, and sometimes this leads to a fatal situation. If it is the case, surgery for removing the acoustic neuroma is needed.

In the surgery, it is important not only to remove the acoustic neuroma as maximum as possible, but also to preserve a function of the cochlear nerve 4c which touches the acoustic neuroma and already suffers from a deformation disorder. Therefore, in the conventional surgery, in order to continuously monitor an auditory (nerve) function, an auditory brainstem response (ABR) needle electrode 7 using a subdermal needle A (see FIG. 9) and a cochlear nerve action potential (CNAP) plate electrode 8 (see FIGS. 10A to 10C) using a plate C, are used as shown in FIG. 6. The ABR needle electrode 7 is attached to a scalp at a rear portion of an ear to be used for auditory brainstem responses (ABRs). The ABR needle electrode 7 monitors the auditory brainstem responses (ABRs) by a scalp needle electrode. Potentials collected at the place where the electrode is attached are displayed on a monitor screen.

For another type of an electrode, the CNAP plate electrode 8 is held on the auditory nerves 4 between the cochlear D and the brainstem E, or inserted into a spot of the auditory nerve 4. A potential detected at this spot is displayed on the monitor screen. Then, by monitoring a waveform displayed on the screen, the surgery is performed by taking care not to change the waveform.

Figure 9:
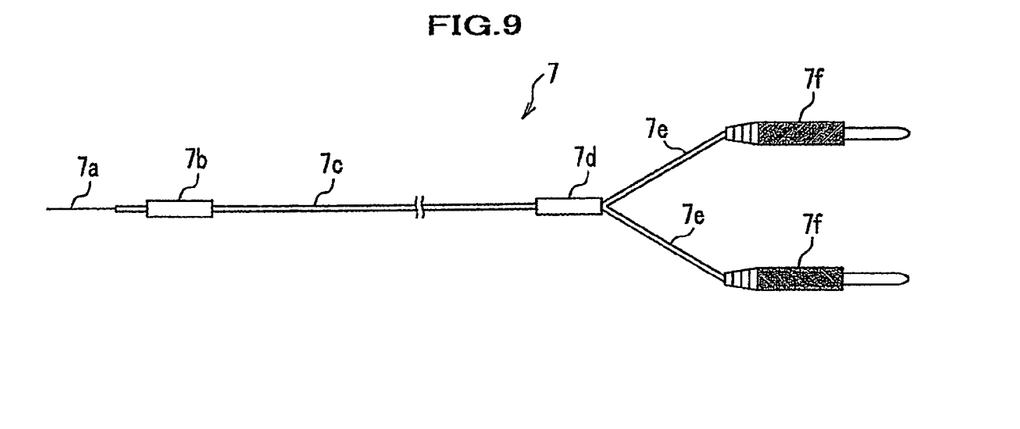
FIG. 9 is a plan view showing a conventional ABR needle electrode.

FIG. 9 is a plan view showing an ABR needle electrode using a conventional subdermal needle. As shown in FIG. 9, at the left edge of the ABR needle electrode 7, the subdermal needle with a φ0.45 mm diameter is provided at a 15 mm length. The electrode 7 is divided to two lead wires 7e of a 20 cm length, through a tube cover 7b, a lead wire 7c of a 60 cm length, and a tube cover 7d. At the right end of the electrode 7, molded pin tips 7f are connected. A total length of the ABR needle electrode 7 is about 1 m.

Figure 10A:
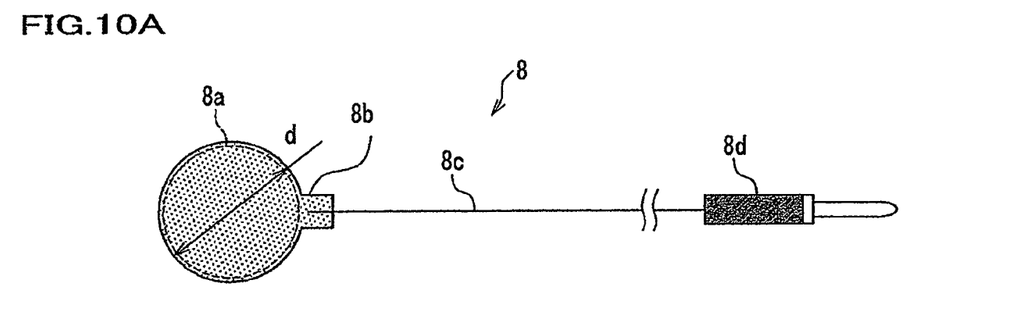
FIG. 10A is a magnified plan view.
Figure 10B:
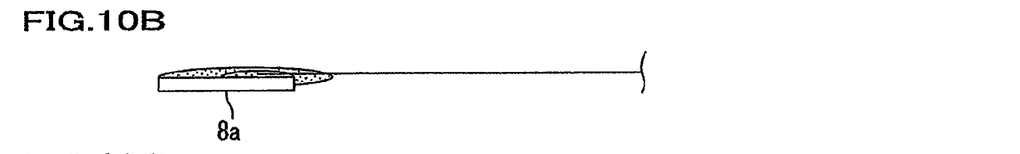
FIG. 10B is a magnified front view.
Figure 10C:
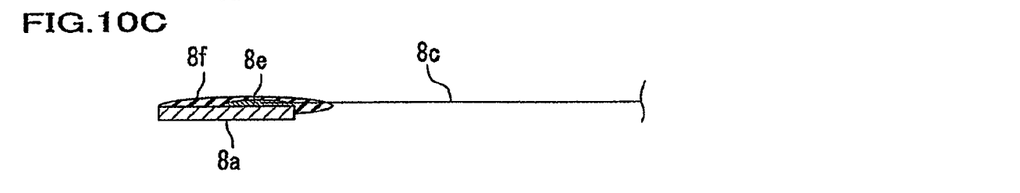
FIG. 10C is a magnified cross sectional view.

FIGS. 10A to 10C show a conventional CNAP plate electrode. FIG. 10A is a magnified plan view. FIG. 10B is a magnified front view. FIG. 10C is a magnified cross sectional view. As shown in FIGS. 10A to 10C, an electrode part 8a of the CNAP plate electrode 8 has a disk shape, of which diameter d is about 2.5 mm. A protrusion part 8b is formed for a gripping part to be used during an insertion. A pin tip 8d is connected to the protrusion part 8b with a lead wire 8c of about 1 m. As shown in FIG. 10C, a material of the electrode 8a is a platinum plate, of which thickness is 0.1 mm. At the rear face (upper face) of the electrode 8, a lead wire 8c is soldered (8e). The upper face of the electrode part 8 is molded by a rapid 8f made of resin in order to reduce background noises.

Figure 11:
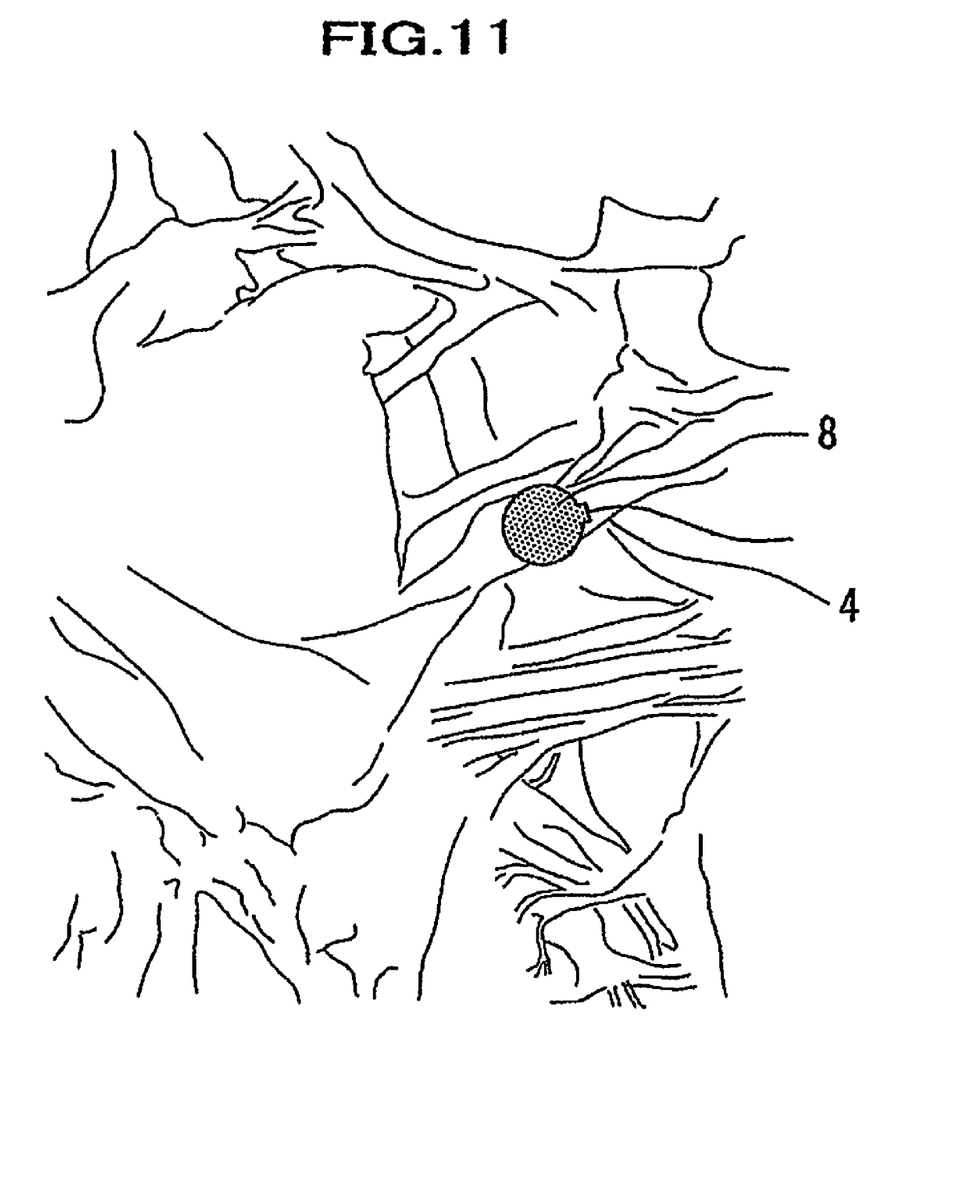
FIG. 11 is a perspective view showing a state that a conventional CNAP plate electrode is held.

FIG. 11 is a diagram showing a state that the CNAP plate electrode 8 is held. As shown in FIG. 11, the CNAP plate electrode 8 is held on the auditory nerve 4.

Figure 8A:
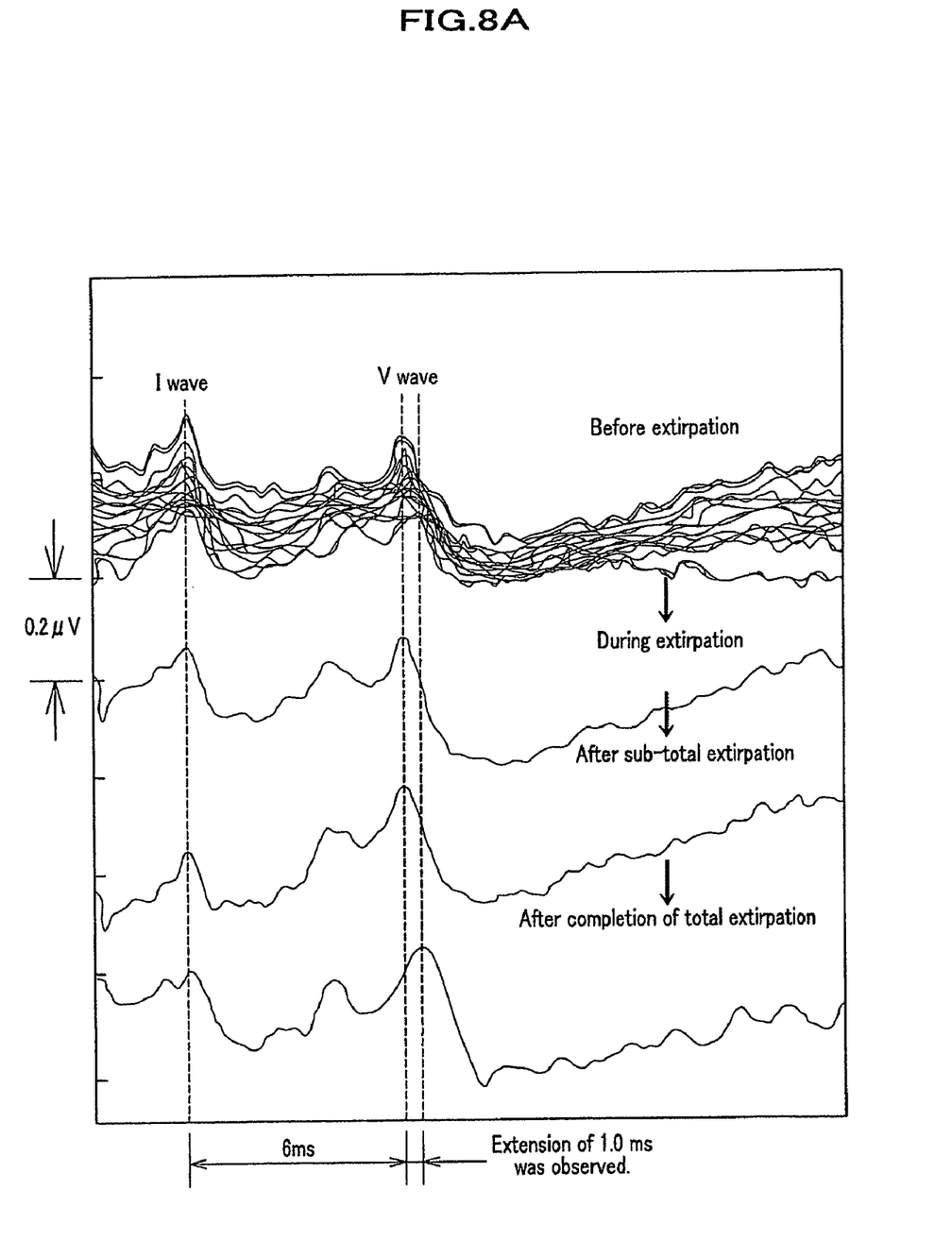
FIGS. 8A and 8B show graphs of waveforms of conventional monitoring images.
Figure 8B:
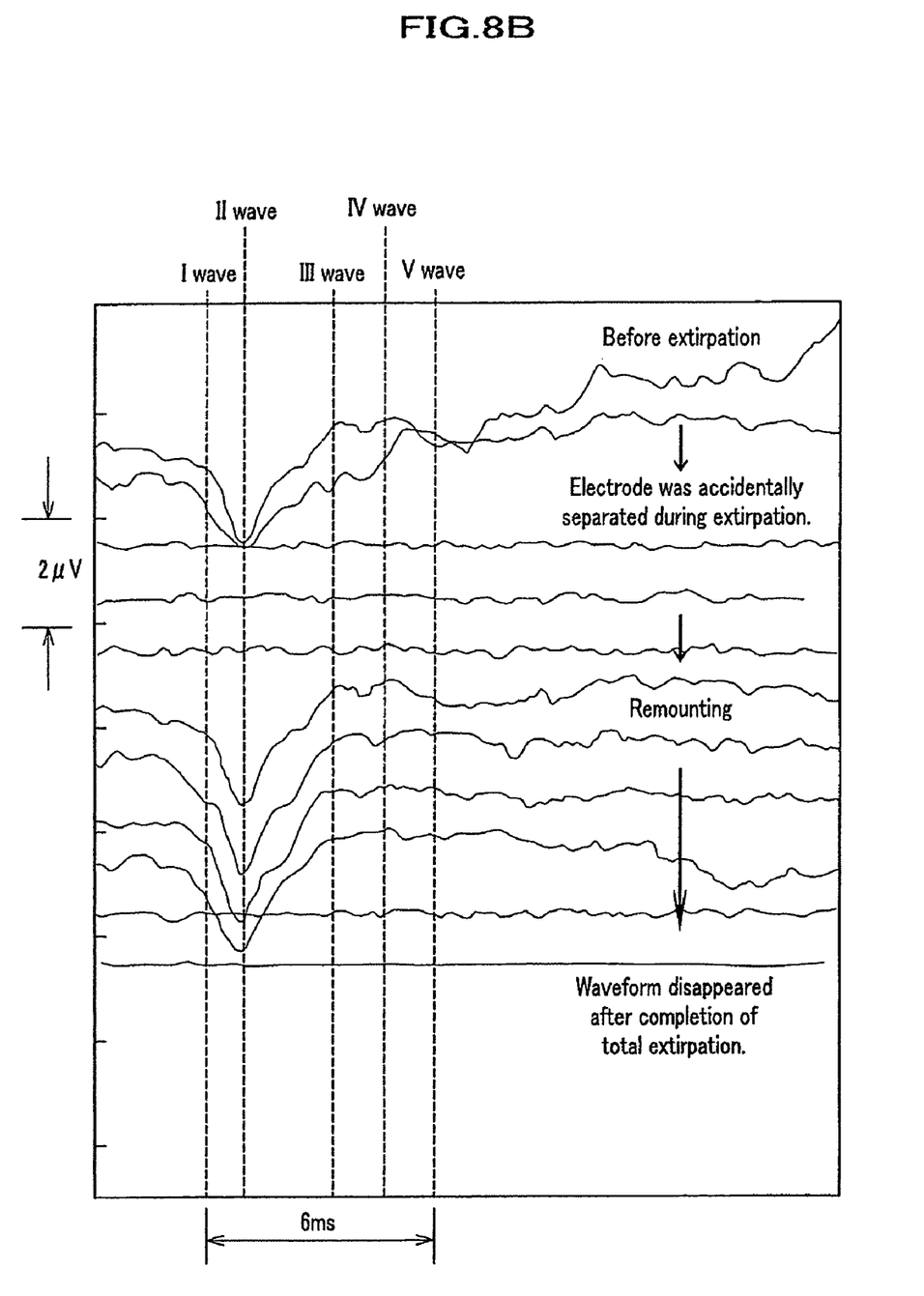
Figure 8C:
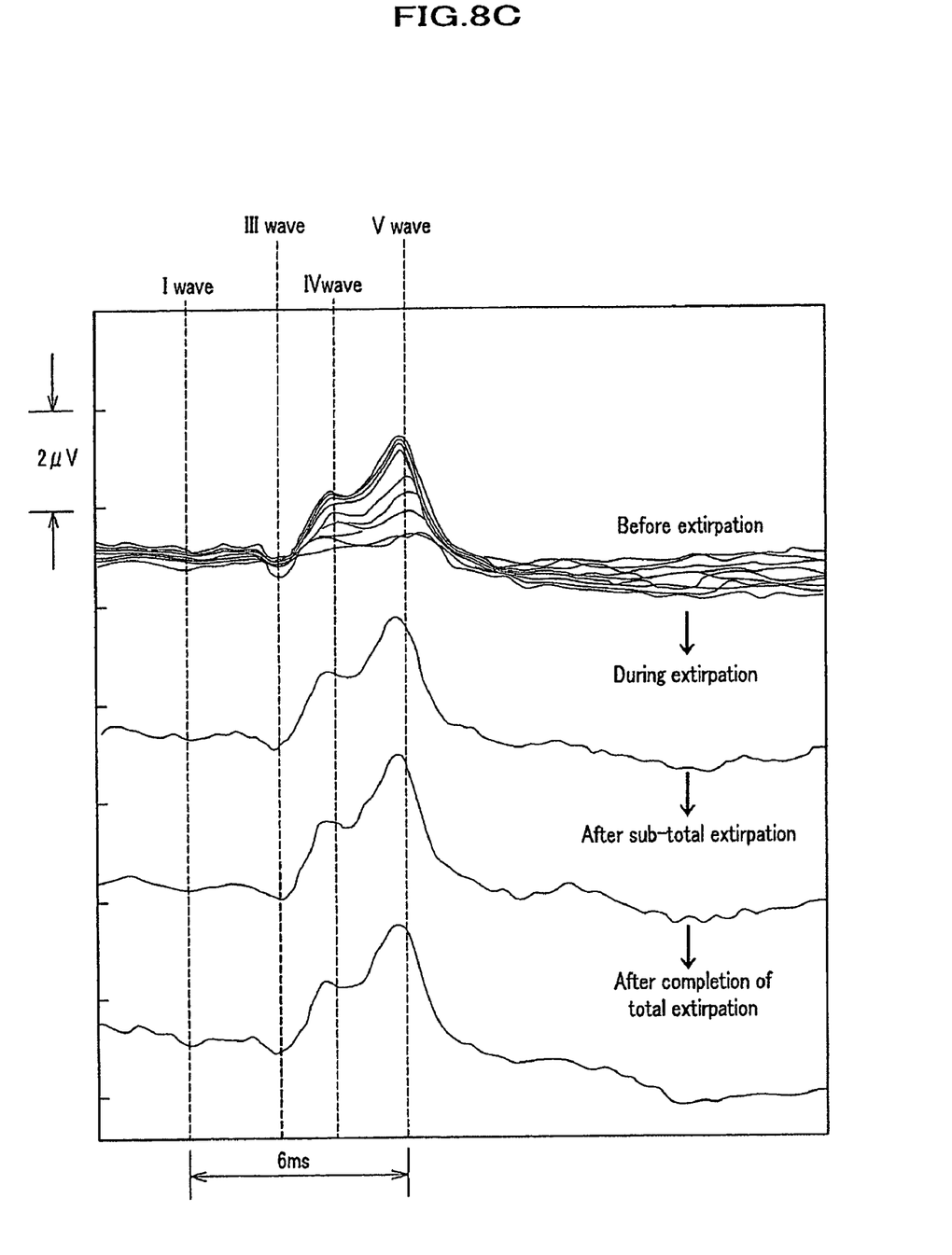
FIG. 8C is a graph of waveforms showing a new monitoring image using the DNAP monitoring electrode 10 of the present invention.

FIGS. 8A to 8C show graphs of potentials measured by conventional electrodes, and a graph of potentials measured by an electrode of the present invention. FIGS. 8A and 8B show graphs of conventional monitoring images measured by the ABR needle electrode and the CNAP plate electrode. FIG. 8C shows a graph of a monitoring image measured by the electrode of the present invention.

As shown in FIG. 8A, the ABR needle electrode is a conventional tool, which is a scalp needle electrode. By using the electrode, auditory brainstem evoked potentials are measured, and the potentials are displayed on a monitor screen as a graph of waveforms. That is, a click sound entered into ears is displayed as a brainwave. The ABR needle electrode can be stably held on a scalp. However, the waveform contains many noises due to a long distance from the brainstem, and the recorded waveform of the auditory evoked potentials is unstable. Therefore, 500 times adding and averaging frequency is needed in order to obtain a reproducible waveform. As a result, 30 seconds are needed to obtain one waveform. Herein, an extension of a latent period of ABR I to V waves is observed in FIG. 8A. By keeping a change (delay) of the latent period of the ABR I to V waves in a predetermined range (within 0.8 ms) during an operation, it is known that cochlear nerve function can be effectively maintained. However, because of unstable monitoring waveforms and too long monitoring time, the ABR needle electrode method is not a satisfied method as a real time monitoring method.

As shown in FIG. 8B, a graph of waveforms measured by the CNAP plate electrode is obtained by measuring the cochlear nerve action potential (CNAP) responses by a method in which the CNAP plate electrode 8 is held on the auditory nerve 4 shown in FIG. 11. The waveforms are recorded by amplifying waveforms corresponding to an ABR II wave, III wave and IV wave. The waveforms do not contain many noises because the electrode is held close to the brainstem, and are obtained as large waveforms having 1 to 2 µV maximum for II to IV waves. About 200 times adding and averaging frequency is needed so as to obtain a reproducible waveform and 12 seconds are needed to obtain one waveform. As shown in FIG. 8B, initially obtained high amplitude waves II to IV are lost after completion of total extirpation. Here, the most critical problem is that the electrode can not be stably held. It is suggested that the method using the CNAP plate electrode 8 becomes a more accurate monitoring method than the ABR needle electrode method, if the CNAP plate electrode can be held stably. Therefore, a drawback of the CNAP plate electrode method resides in a stability of waveforms when it is used in each operation.

As mentioned above, the ABR needle electrode 7 held on a scalp provides small waveforms due to a potential attenuation caused by a long distance from the brainstem E. Further, many background noises which occur at a lead wire (electric cord) of the ABR needle electrode 7 are mixed in the waveforms. Thus, a problem of the ABR needle electrode is that it is difficult to analyze the waveforms.

Further, another type of the electrode, the CNAP plate electrode 8, has problems such as extreme instability for attaching the electrode, difficulty in stable fixing, dropping, and shifting from a measuring position, even if it is held on thread shaped nerves with about 2 mm diameter, or is held between the nerves.

For these reasons mentioned above, a need exists for a monitoring electrode and a monitoring device which can easily and surely measure waveforms with less noises and have a superior performance in accuracy, adherent property, comprehensiveness, recording sensitivity, and recording specificity, than conventional monitoring methods such as the ABR electrode method for monitoring auditory evoked potentials from a skin and the CNAP electrode method for monitoring the potentials just on nerves.

SUMMARY OF THE INVENTION

From a viewpoint as mentioned above, the present invention has been developed to solve these problems hereinbefore. It is an object of the present invention to provide an auditory evoked potential monitoring electrode for monitoring dorsal cochlear nucleus action potentials which has a superior performance in accuracy, adherent property, comprehensiveness, recording sensitivity, and recording specificity required for the auditory evoked potential monitoring electrode. Further, it is another object to provide an auditory evoked potential monitoring electrode by which stable monitoring is easily achieved. Furthermore, it is another object to provide an auditory evoked potential monitoring device for monitoring the dorsal cochlear nucleus using the auditory evoked potential monitoring electrode thereof.

Figure 3A:
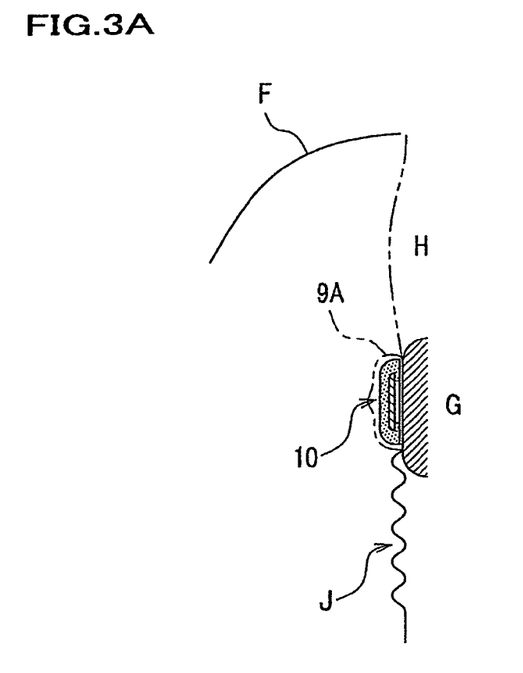
FIG. 3A is a magnified cross sectional view of Y-Y line shown in FIG. 2B.
Figure 3B:
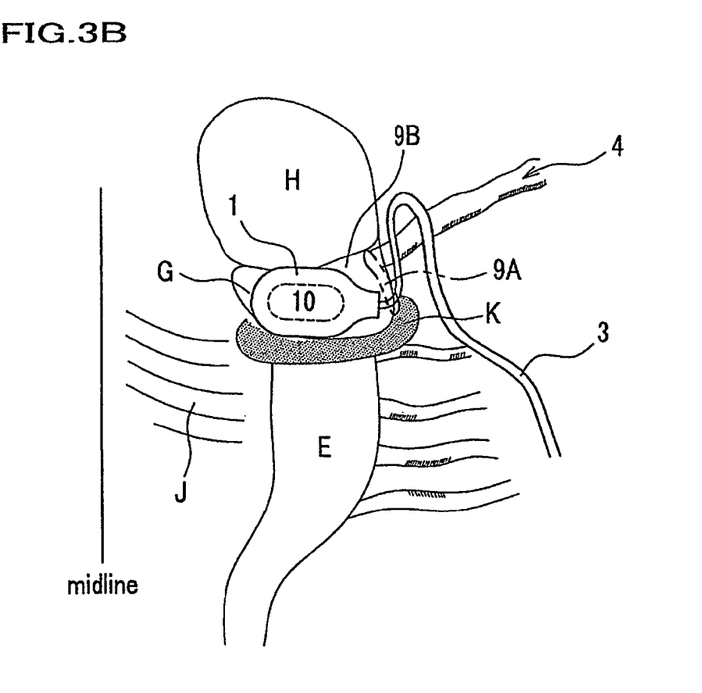
FIG. 3B is a magnified dorsal upper view of the floor of the forth ventricle J after removal of the cerebellar peduncles H.

In order to solve the above-mentioned problems, the present invention includes a monitoring electrode for monitoring dorsal cochlear nucleus action potentials 10 which is held in brain surgery by developing a plane between a proximal portion of the cochlear nerve and a choroid plexus K as shown in FIG. 3B. The cochlear nerve is followed medially as it enters the lateral recess 9B of the fourth ventricle. Confirmation of a foramen of Luschka 9A is made by observing an outflow of spinal fluid. The tenia of the fourth ventricle is elevated and the monitoring electrode 10 is placed into the lateral recess 9B over a surface of the dorsal cochlear nucleus G, which is inside a gap between the peduncle H and the floor of the forth ventricle J. Verification of appropriate holding of the monitoring electrode 10 is conducted by measuring the action potentials. The monitoring electrode 10 comprises an electrode unit 1 for detecting the action potentials, a covering unit 2 which is formed by covering the electrode unit 1 with a biocompatible resin having an exposed face 1a on the electrode unit 1. A round part 2a is provided on the electrode unit 1 to easily insert the electrode unit 1 through the foramen of Luschka 9A. Herein, an outer diameter shape of the covering unit 2 has a width W1 in a range of 3.0 mm to 3.5 mm and a length L1 in a range of 5.5 mm to 10 mm to fit to the gap mentioned above, and the covering unit 2 is formed as covering the electrode unit 1 with protruding from a periphery of the electrode unit 1 to cover both front and rear faces of the electrode unit 1.

As mentioned above, the exposed face 1a for detecting the action potentials can be stably held on the dorsal cochlear nucleus G by fitting an outer diameter shape of the covering unit 2 into the gap between the peduncle H adjacent to the dorsal cochlear nucleus G and the floor of the forth ventricle J.

By having the width W1 which fits to the gap be in a range of 3 mm to 3.5 mm, a very sensitive and specific auditory evoked potential measurement can be achieved because the width can fit to a size just settling on the dorsal cochlear nucleus G. Further, since the covering unit 2 protrudes from the electrode unit 1, the electrode unit 1 can easy fit into the gap between the peduncle H and the floor of the forth ventricle J due to softness of a protruding part. Furthermore, since an outer periphery of the electrode unit 1 does not directly contact to the peduncle and the floor of forth ventricle, it is always achievable to prevent an injury to the peduncle and the floor of the forth ventricle.

Moreover, it is possible to increase a monitoring performance in accuracy, adhesive property, comprehensiveness, recording sensitivity, and recording specificity because the action potentials can be measured directly on the dorsal cochlear nucleus G.

Further, the present invention includes the monitoring electrode for monitoring the dorsal cochlear nucleus action potentials 10, in which the exposed face 1a has a width W2 in a range of 0.5 mm to 3.0 mm and a length L2 in a range of 0.5 mm to 5.5 mm to fit to a region of the dorsal cochlear nucleus G.

Furthermore, the present invention includes the monitoring electrode for monitoring the dorsal cochlear nucleus action potentials 10, in which an outer diameter shape of the covering unit 2 is formed in an oval shape and the exposed face 1a has also an oval shape.

By forming an outer peripheral shape of the monitoring electrode for monitoring the dorsal cochlear nucleus action potentials in an oval shape, it is possible to easily insert the monitoring electrode 10 through the foramen of Luschka 9A, to stably hold it on the dorsal cochlear nucleus G, and to use it for both right and left side ears. Further, by forming the exposed face 1a in the same oval shape as the covering unit 2, it is possible to have a wide exposed face.

Further, the present invention includes the monitoring electrode for monitoring the dorsal cochlear nucleus action potentials 10, in which the biocompatible resin is made of silicon. Since the biocompatible resin of the covering unit 2 of the monitoring electrode 10 is formed of silicon, the monitoring electrode 10 can softly contact with a measuring part as softly as the floor of the forth ventricle.

The present invention includes: a monitoring device for monitoring the dorsal cochlear nucleus action potentials 16 including the monitoring electrode for monitoring the dorsal cochlear nucleus action potentials 10; a sound stimulator 6a for stimulating an auditory sense of a patient on whom the monitoring electrode for monitoring the dorsal cochlear nucleus action potentials 10 is held; a display 6b for displaying action potentials detected by the monitoring electrode for monitoring the dorsal cochlear nucleus action potentials 10; an amplifier for excluding noises mixing in the same phase; and an A/D converter for converting an analogue signal to a digital signal.

The monitoring device for monitoring the dorsal cochlear nucleus action potentials is improved so that a performance in accuracy, recording sensitivity and recording specificity is improved in accordance with an information flow, and a sharp waveform which is easily analyzed can be obtained by reducing background noises and making the waveform clear.

Actually, an adding and averaging frequency to obtain a reproducible waveform comes to only 50 times and one recording every three seconds becomes possible. Virtually, a real time monitoring of a cochlear nerve action and an auditory function becomes available for the first time by the present invention. Further, stability of the electrode is excellent, and any slipping and recording problems after the insertion of the electrode have not been observed in more than 50 cases treated so far.

The monitoring electrode for monitoring the dorsal cochlear nucleus action potentials (hereinafter, referred to DNAPs) of the present invention and a DNAP monitoring device using the DNAP monitoring electrode can improve a performance needed for an auditory evoked potential monitoring electrode, in accuracy, adherent property, comprehensiveness, recording sensitivity, and recording specificity. In addition, the DNAP monitoring electrode and the DNAP monitoring device can be easily and stably held, and reduce background noises.

BRIEF DESCRIPTION OF THE DRAWINGS

FIGS. 1A to 1D show a monitoring electrode for monitoring dorsal cochlear nucleus action potentials (DNAPs) 10 of the present invention.

FIGS. 7A and 7B are magnified cross sectional views showing an auditory nerve 4 in a right internal auditory canal.

FIGS. 10A to 10C show a conventional CNAP plate electrode.

DETAILED DESCRIPTION OF THE PREFERRED EMBODIMENTS

Figure 1A:
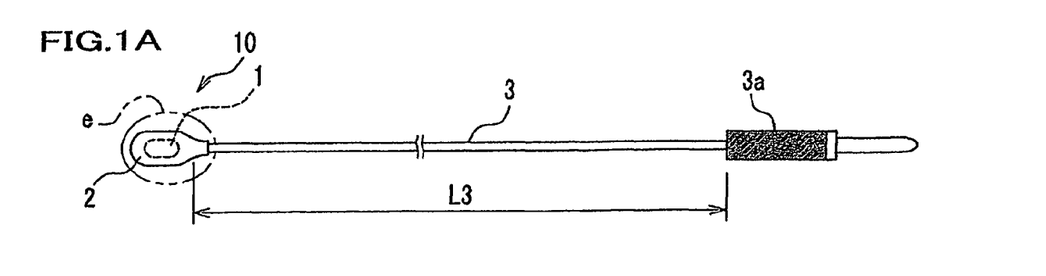
FIG. 1A is a plan view showing a whole structure of the monitoring electrode 10.
Figure 1B:
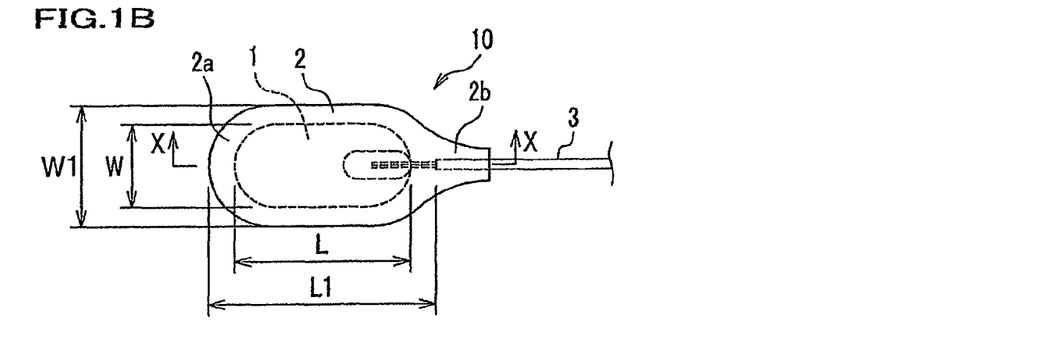
FIG. 1B is a magnified plan view of an e-part shown in FIG. 1A.
Figure 1C:
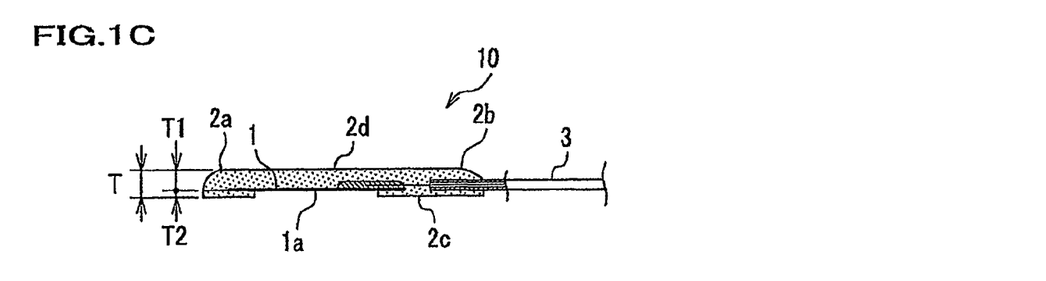
FIG. 1C is a magnified cross sectional view of X-X line shown in FIG. 1B.
Figure 1D:
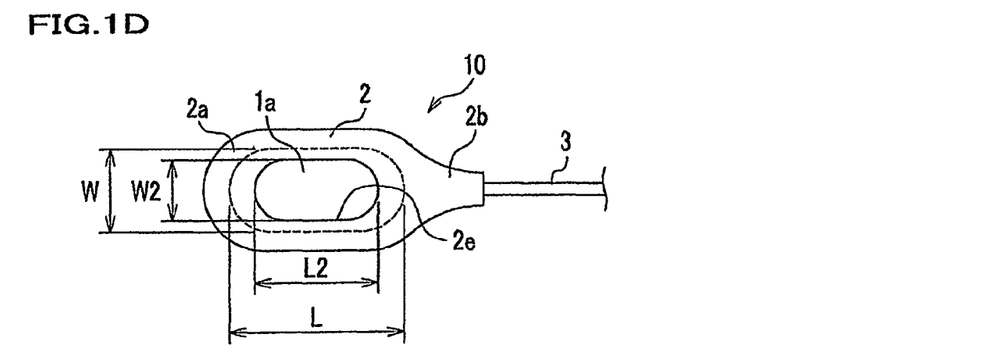
FIG. 1D is a magnified bottom view of the monitoring electrode 10.
Figure 2A:
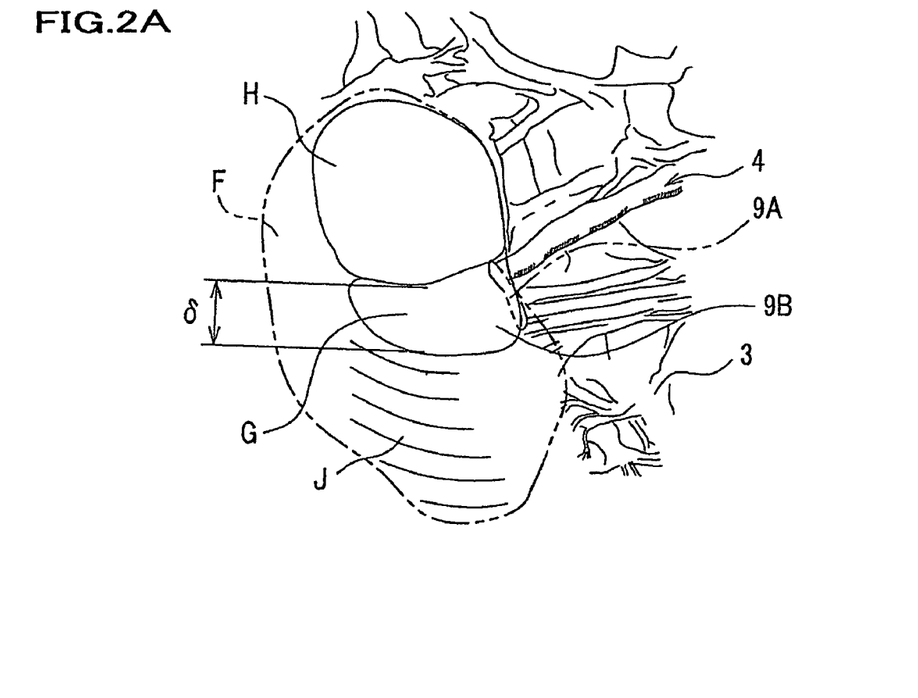
FIG. 2A is a magnified view showing a position of a dorsal cochlear nucleus G.
Figure 2B:
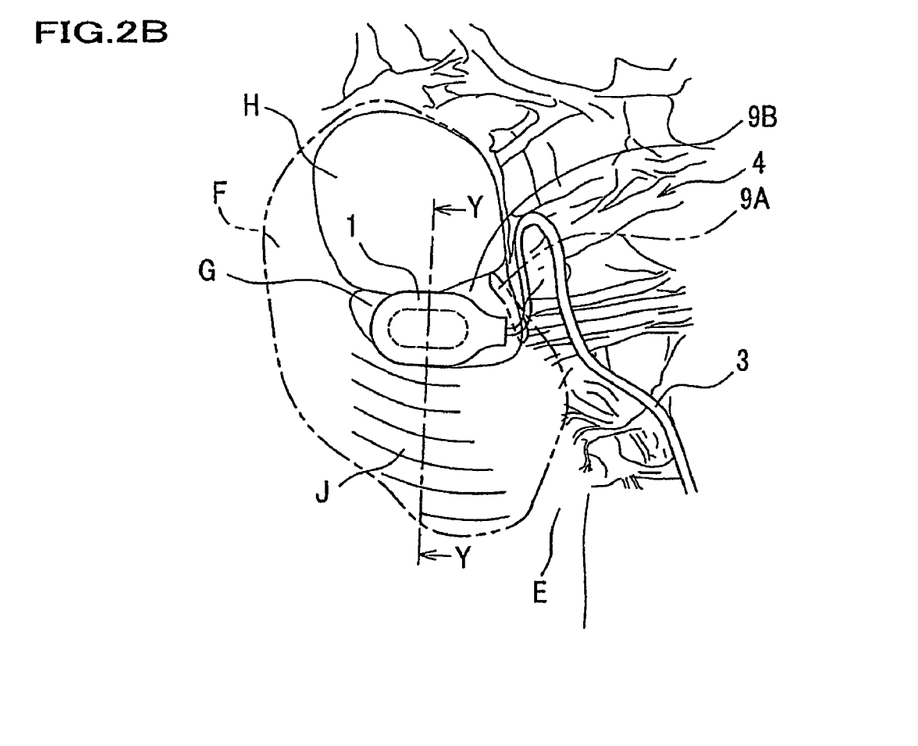
FIG. 2B is a magnified view showing a state that the DNAP monitoring electrode 10 is held on the dorsal cochlear nucleus G.

The DNAP (Dorsal cochlear Nucleus Action Potential) monitoring device for monitoring the DNAPs of the present embodiment will be explained in detail in reference to associated drawings. FIGS. 1A to 1D show the DNAP monitoring electrode for monitoring the DNAPs of the present invention. FIG. 1a is a plan view showing a whole structure of the monitoring electrode. FIG. 1B is a magnified plan view showing an e-part shown in FIG. 1A. FIG. 1C is a magnified cross sectional view of X-X line shown in FIG. 1B. FIG. 1D is a magnified bottom view of the monitoring electrode. FIG. 2A is a magnified view showing a position of the dorsal cochlear nucleus. FIG. 2B is a magnified view showing a state that the DNAP monitoring electrode is held on the dorsal cochlear nucleus. FIG. 3A is a cross sectional view of Y-Y line shown in FIG. 2B. FIG. 3B is a magnified dorsal upper view of the floor of the forth ventricle after removal of the cerebellar peduncles H shown in FIG. 2B.

As shown in FIG. 1A, the DNAP monitoring electrode 10 comprises: an electrode unit 1 for detecting action potentials of the dorsal cochlear nucleus; a covering unit 2 which is formed by having an exposed face 1a (see FIG. 1C) on the electrode unit 1 and covering the electrode unit 1 with a biocompatible resin; an electrode wire 3 (lead wire) connected to the electrode unit 1; and a pin tip unit 3a.

Position of Dorsal Cochlear Nucleus

As shown in FIG. 2A, the dorsal cochlear nucleus G is clearly discernible as a bulging at the floor of the forth ventricle J. The dorsal cochlear nucleus G extends diagonally from the mediorostral to laterocaudal area in the rostral portion of the foramen of Luschka 9A. In other words, the dorsal cochlear nucleus G is located in a gap between the peduncle H and the floor of the forth ventricle. The electrode unit 1 covered with the covering unit 2 of the DNAP monitoring electrode 10 is inserted through the foramen of Luschka 9A and held on the dorsal cochlear nucleus G.

Material of Electrode Unit

As shown in FIG. 1C, the electrode unit 1 detects the action potentials of the dorsal cochlear nucleus, and is formed in an oval shape. A material of the electrode unit 1 is platinum (Pt)

foil. On the electrode unit 1, the covering unit 2 which is formed by covering the electrode unit 1 with a biocompatible resin is arranged, and an oval exposed face 1a is formed to detect the action potentials.

Size of Electrode Unit

As shown in FIGS. 1B and 1D, a size of the electrode unit 1 has a width W: W1>W>W2, and a length L: L1>L>L2. In the present embodiment, for example, the width W of the electrode unit 1 is 2.0 mm, and the length L thereof is 4.5 mm.

That is, the width W of the electrode unit 1 is made so that it is smaller than the gap δ shown in FIG. 2A and smaller than the foramen of Luschka 9A.

Size of Exposed Face of Electrode Unit

As shown in FIG. 1D, a size of the exposed face 1a of the electrode unit 1 is as follows: a width W2 is 1.5 mm; a length L2 is 3.0 mm. Similar to the electrode unit 1, the exposed face 1a has an oval shape. The exposed face 1a is prepared only on the front face (bottom side in FIG. 1C). A whole surface of the rear face (upper side in FIG. 1C) is covered by a biocompatible resin.

As a result, a size of the exposed face 1a is made to fit to a region of the dorsal cochlear nucleus G from a viewpoint of recording sensitivity and recording specificity so that the action potentials are stably and highly accurately measured by attaching the exposed face 1a on a surface of the dorsal cochlear nucleus G.

If there is a curved portion in the electrode unit 1, this has an effect on sensitivity and accuracy to corrupt them. Hereby, the electrode unit 1 is made to have a suitable rigidity. Therefore, a periphery of the electrode unit 1 is covered by the covering unit 2 because the electrode unit 1 may injure the peduncle H and the floor of the forth ventricle J, if the periphery of the electrode unit 1 is exposed.

Construction of Covering Unit

As shown in FIG. 1C, the covering unit 2 covers the whole electrode unit 1 and holds the periphery of the electrode unit 1 as wrapping it. The covering unit 2 has an oval shape with a size to fit to a shape of the dorsal cochlear nucleus G, comprising a round part 2a, a handle part 2b, and an opening part 2e.

As shown in FIG. 2B, an outer diameter shape of the covering unit 2 has a width W1 (see FIG. 1B) which fits to a gap δ between the peduncle H adjacent to the dorsal cochlear nucleus G and the floor of the forth ventricle J.

More specifically, it is needed that the outer diameter shape of the covering unit 2 has a size of the width W1 so that the monitoring electrode is stably held in the gap δ, and that the monitoring electrode can be inserted through the foramen of Luschka 9A. If the width W1 of the covering unit 2 is too large, the monitoring electrode can not be held in the gap δ and can not be inserted through the foramen of Luschka 9A. If the width W1 is too small, it may cause a reduction of measuring accuracy because the monitoring electrode can easily shift in the gap δ. As mentioned-above, by making the width W1 of the covering unit 2 have a size to fit to the gap δ, the exposed face 1a can be held on the dorsal cochlear nucleus G in a stable state.

Further, by fitting the outer diameter shape of the covering unit 2 to the same shape analogous to the shape of the dorsal cochlear nucleus G, it is possible that the monitoring electrode can be continuously, stably held at a position after it was held. Furthermore, by making the size of the covering unit 2 minimum, the monitoring electrode can be easily inserted corresponding to restrictions in the size of the foramen of Luschka 9A (foramen opened naturally).

Material of Covering Unit

The covering unit 2 is made of a biocompatible resin. The biocompatible resin is formed of, for example, silicon (or called silicone). The silicon is aggregates formed of organo-silicon compounds and has a sufficient elasticity like rubber. Therefore, the covering unit 2 can fit to a size of the gap between the peduncle H and the floor of the forth ventricle J. Further, since the silicon covers the electrode unit protruding from a periphery thereof, the protruding part can flexibly fit to the gap between the peduncle H and the floor of the forth ventricle J. Furthermore, the silicon is softer than a resin (formed by a rapid prototyping forming) and as soft as the peduncle H and the floor of the forth ventricle J. The silicon has a character that it adheres to a surface of the dorsal cochlear nucleus like a sucker. Furthermore, in place of the silicon, the covering unit 2 may be made of a polyurethane resin, soft plastic, and rubber which are as elastic and soft as the silicon.

The round part 2a, as shown in FIG. 1D, is formed in a round and arc shape so that the DNAP monitoring electrode 10 can be easily inserted through an opening foramen of Luschka 9A (see FIGS. 3A, 3B) by a special and unique shaped pair of tweezers. In this regard, the round part 2a may be formed in an arc shape by connecting two rectangular corners of the electrode.

The handle part 2b may be formed in an R shaped (arc shaped) and S curved streamline shape covering up to an electrode wire 3 so that the DNAP monitoring electrode 10 can be easily taken out through the foramen of Luschka 9A.

By forming the handle part 2b in the shape as mentioned above, it is possible to easily attach the electrode because the handle part 2b is easily held by the pair of tweezers.

Size of Covering Unit

With respect to a size of the covering unit 2, as shown in FIG. 1B, a width W1 is 3.0 mm and a length L1 is 5.5 mm, and as shown in FIG. 1C, a thickness T is 0.4 mm. Regarding the thickness T, a thickness T1 is 0.3 mm, and a thickness T2 is 0.1 mm. The electrode unit is buried between the covering parts with T1 and T2.

A maximum size of the covering unit 2 is limited by a size for fitting to a region of the dorsal cochlear nucleus G. A width W1 is 3.5 mm and a length L1 is 10 mm. Since there is no insertion route except for the foramen of Luschka 9A, the width W1 is specifically limited. Here, the width W1 may be in a range of 2.5 mm to 3.5 mm, preferably, in a range of 3.0 mm to 3.5 mm.

In the embodiment, a diameter of the electrode wire 3 is φ0.4 mm, preferably, is in a range of φ0.3 mm to 0.5 mm. The electrode wire 3 is covered with a green isolator. A length L3 of the electrode wire 3 is just 1 m, or may be longer or shorter than 1 m.

A pin tip 3a is a plug, which is connected to a connecting terminal of the monitoring device for monitoring the DNAPs 16 as mentioned hereinafter.

Accordingly, as shown in FIG. 1D, an exposed face is prepared widely by forming: an outer diameter shape of the covering unit 2 oval, an outer diameter of the electrode unit 1 oval, and the exposed face 1a formed by the opening part 2e oval. Further, the exposed face 1a has a size for widely fitting to a region of the dorsal cochlear nucleus G. As mentioned above, by making the size fit to the region, reliability of data is warranted with improving a performance of required sensitivity and accuracy. Furthermore, the monitoring electrode can be commonly used at right and left sides by forming the shape oval. It is not needed to increase the number of types to manufacture, for example, a left side type (left hand) of the dorsal cochlear nucleus G and a right side type (right hand) of the dorsal cochlear nucleus G.

Next, a method for holding the DNAP monitoring electrode 10 will be explained.

As shown in FIGS. 2A and 2B, the auditory nerve 4 and a facial nerve 5 are formed directed to a brainstem E at the right side of the drawing. The brainstem E near the nerves is covered by a cerebellum F. At the bottom of a gap between the peduncle H and the floor of the forth ventricle J, which is the hidden gap, the dorsal cochlear nucleus G is located. Here, surgery of placing the monitoring electrode 10 is conducted by observing a right position under a microscope.

FIG. 3A is a magnified cross sectional view of Y-Y line in FIG. 2B. As shown in FIG. 3A, inside the gap between the peduncle H and the floor of the forth ventricle J, the dorsal cochlear nucleus G is located. A size of the DNAP monitoring electrode 10 is determined so as to fit to a region of the dorsal cochlear nucleus G. This region is only a place available for holding the monitoring electrode 10. As shown in FIG. 3B, the DNAP monitoring electrode 10 is inserted from the foramen of Luschka 9A into a lateral recess 9B to be held in a bottom of the narrow gap. If the size of the DNAP monitoring electrode 10 is smaller than the gap, the electrode floats in entering water and shifts in the valley resulting in increase in background noises. Thus, a suitable weight and size are needed for the electrode. On the other hand, if the size of the electrode is large, it is impossible to insert the electrode because the foramen of Luschka 9A is small, from which the DNAP monitoring electrode 10 is inserted. As a result the size of the DNAP monitoring electrode 10 is obviously specified. If the DNAP monitoring electrode 10 has the specified size as mentioned above, it is possible to record the action potentials accurately and sensitively with covering the region of the dorsal cochlear nucleus G and collecting nearly all the electric action since the DNAP monitoring electrode 10 is not shifted on the surface of the dorsal cochlear nucleus G.

As shown in FIGS. 3A and 3B, the method for holding the DNAP monitoring electrode 10 is comprised of: inserting the DNAP monitoring electrode 10 from the foramen of Luschka 9A by a specified pair of tweezers; further inserting the DNAP monitoring electrode 10 through the lateral recess 9B along a (right) glossopharyngeal nerve by moving the cerebellum F; and holding the DNAP monitoring electrode 10 on the surface of the dorsal cochlear nucleus G adherent with the cerebellum F so as to cover the whole region of the dorsal cochlear nucleus G in the gap between the peduncle H and the floor of the forth ventricle J. Accordingly, the DNAP monitoring electrode 10 is held by being pressed by the cerebellum F onto the floor of the forth ventricle J.

Hereby, the DNAP monitoring electrode 10, which is a plate electrode, is stably held on the dorsal cochlear nucleus G located at the brainstem E. As a result, it is possible to measure clear action potentials with extremely reducing background noises because a source of the action potentials is based on the brainstem E.

The above-mentioned outstanding effect can not be achieved by conventional electrodes (ABR subdermal needle electrode 7 and CNAP plate electrode 8). The present invention has been developed through a series of repeated studies on a shape and material of the electrode to fit to the dorsal cochlear nucleus G at the brainstem E, and manufacturing trials. At last, the present invention gets to a goal of producing the monitoring electrode for monitoring the dorsal cochlear nucleus action potentials (DNAPs), and the monitoring device for monitoring the DNAPs using the monitoring electrode thereof on a commercial basis.

Accordingly, the present invention succeeds in obtaining the action potentials directly from the dorsal cochlear nucleus G at the brainstem E by the most preferable electrode capable of fitting to the dorsal cochlear nucleus G, and in obtaining the action potentials having no background noises in a high-performance manner. Hereby, it becomes possible to conduct otolaryngology and neurological surgery based on the more highly accurate action potentials in future surgery. As a result, the present invention can provide a remarkable effect of preventing a patient from losing or worsening the auditory function in a high probability.

The DNAP monitoring electrode 10 is an epoch-making invention to achieve improvement of all performances in accuracy, adherent property, comprehensiveness, recording sensitivity, and recording specificity in comparison with performance of the conventional electrodes.

FIG. 8C is a graph of waveforms showing a new monitoring image using the DNAP monitoring electrode of the present invention. As shown in FIG. 8C, waveforms are recorded by amplifying waveforms which correspond to ABR III wave, IV wave and V wave. The waveforms are very stable and the recording is performed stably throughout the procedure. Here, potentials of DNAP III to V waves are in a range of 3.0 μV to 4.0 μV in maximum, which are about 20-fold to 30-fold higher than those of conventionally measured waves. A unit of the scale of the DNAP represents 2.0 μV similar to that of the CNAP, which is 10-fold higher than that of the ABR, showing the high performance of the monitoring electrode of the invention.

The above mentioned ABR is liable to be influenced by background noises. In contrast, the DNAP provides a smooth waveform constantly, of which potential is 2 μV similar to the CNAP and is 10 times higher than that of the ABR.

As mentioned above, it is a novel and undeveloped holding method in the medical industry to hold the DNAP monitoring electrode 10 on the dorsal cochlear nucleus G in itself. The monitoring method is uniquely novel. Further, the DNAP monitoring electrode 10 held on the dorsal cochlear nucleus G provides a remarkable effect as shown in Table 1 described hereinafter. Hereinbefore, the embodiment has been explained as the DNAP monitoring electrode 10 is held covering a whole region of the dorsal cochlear nucleus G. However, the DNAP monitoring electrode 10 can be held covering the partial region of the dorsal cochlear nucleus G.

Table 1 is a comparative table to compare recording conditions of the respective monitoring electrodes. Table 1 clearly shows an outstanding effect of the DNAP monitoring electrode 10 of the present invention.

TABLE 1

| recording conditions | ABR | CNAP | DNAP |
|---|---|---|---|
| average adding frequency | 500-1000 | 100-500 | 50-200 |
| one adding time (17 Hz) | 60 ms | 60 ms | 60 ms |
| total adding time | 29 s/500 times | 6 s/100 times | 3 s/50 times |
| sensitivity | 5-10 μV/DIV | 100 μV/DIV | 100 μV/DIV |
| filter | 200-1000 Hz | 200-1000 Hz | 200-1000 Hz |

TABLE 2

| recording conditions | ABR | CNAP | DNAP |
|---|---|---|---|
| stimulus type | sound stimulus | sound stimulus | sound stimulus |
| stimulus width | 50 msec | 50 msec | 50 msec |
| stimulus frequency | 10-20 Hz | 10-20 Hz | 10-20 Hz |
| stimulus waveform | click sound | click sound | click sound |
| stimulus strength | 90-105 dB | 90-105 dB | 90-105 dB |

It is obvious that a performance of the DNAP monitoring device 16 such as an average of adding frequency, a total adding time, and sensitivity is greatly improved in comparison with conventional monitoring devices. Further, in an operation, weak and unstable action potentials of the cochlear nerve, which have been regarded as impossible to be constantly observed, becomes capable of being sharply and sensitively observed by the DNAP monitoring device using the DNAP monitoring electrode 10. As a result, a success rate of preserving an auditory function is greatly improved in an operation of the acoustic neuroma.

Here, a manufacturing method of the DNAP monitoring electrode 10 will be explained.

Figure 4A:
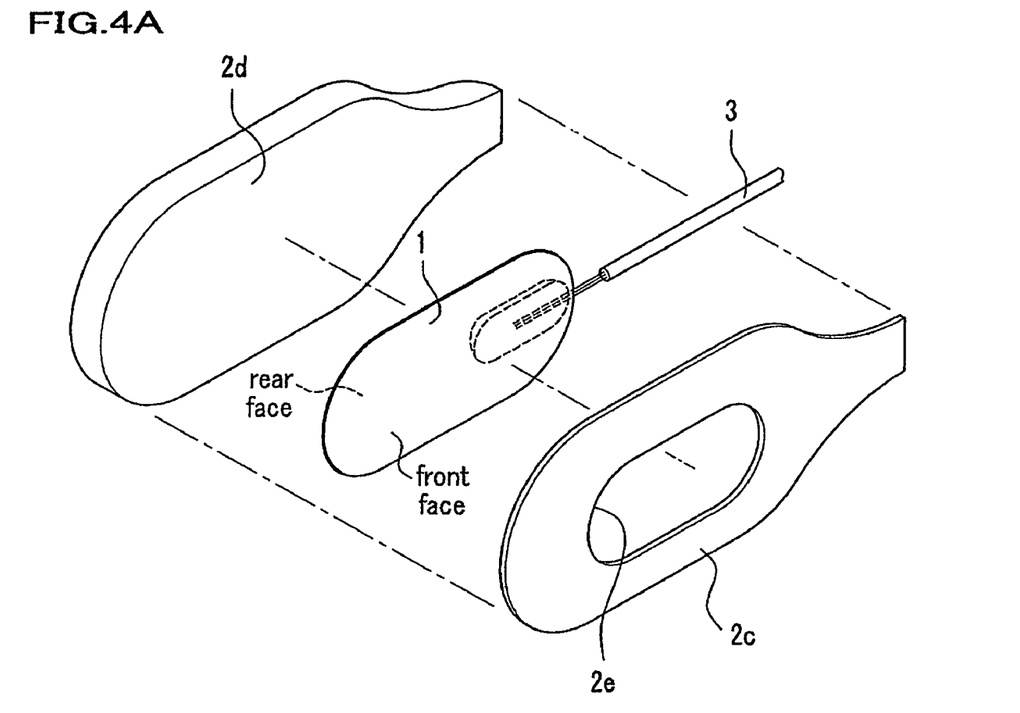
FIG. 4A is an explanatory diagram showing first, second, third and forth manufacturing processes.
Figure 4B:
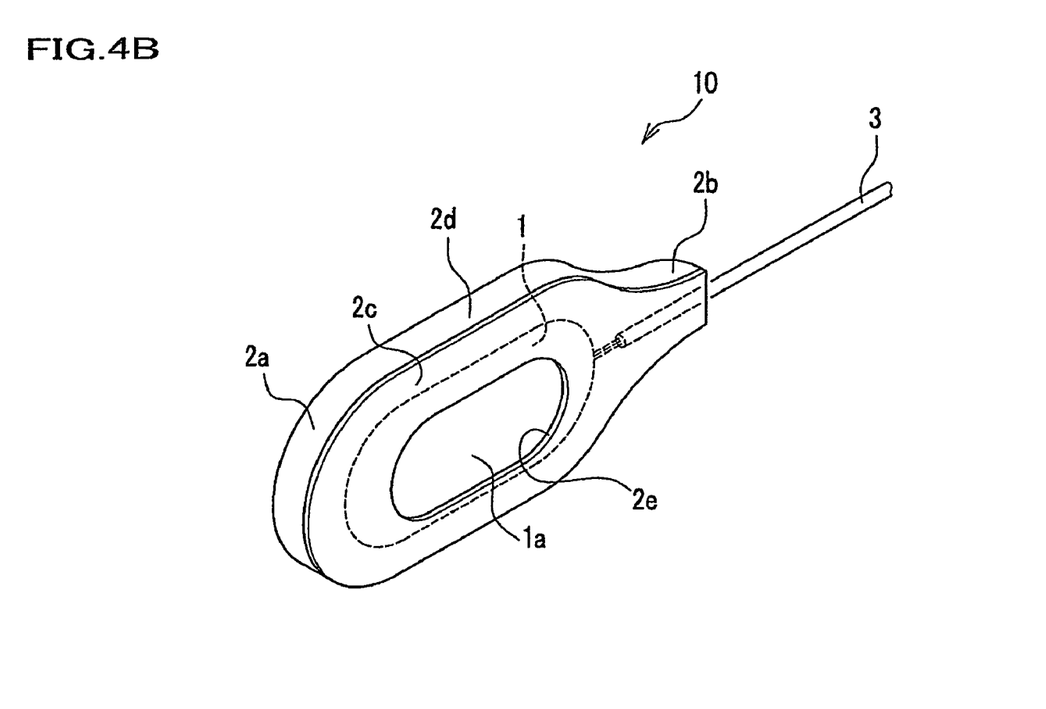
FIG. 4B is a perspective view showing a fifth process combining the above four processes.

FIG. 4A is a perspective view showing first, second, third and forth processes. FIG. 4B is a perspective view showing a fifth process combining these four processes.

The first process is, as shown at a center of FIG. 4A, a step of forming the electrode of a platinum foil plate in an oval shape.

The second process is, as shown at a center of FIG. 4A, a step of connecting the electrode wire 3 to the rear face of the electrode unit 1 (back side of the view) by soldering. With respect to the connecting method, a method using a conducting adhesive and other methods can be used.

The third process is, as shown in FIG. 4A, a step of forming a biocompatible resin back plate 2d in an oval shape larger than the electrode 1, which is a part of the covering unit 2 on the rear face of the electrode unit 1

The forth process is, as shown in FIG. 4A, is a step of forming a biocompatible resin front plate 2c in an oval shape larger than the electrode 1 similar to the third method, which is the covering unit 2 for the front face of the electrode unit 1. In addition, the forth process prepares an oval shaped opening part 2e in the covering unit 2 and an exposed face 1a (see FIG. 4B) on the electrode unit 1.

The fifth process is, as shown in FIG. 4B, a step of attaching the electrode unit 1 on which the electrode wire is connected to the rear face, between the biocompatible resin back plate 2d and the biocompatible resin front plate 2c, and bonding the unit and plates together.

In this way, a whole electrode unit 1 is covered with silicon by being held between the biocompatible resin back plate 2d which is the covering unit 2 for the rear face and formed in a larger oval shape than that of the electrode 1, and the biocompatible resin front plate 2c which is the covering unit 2 for the front face.

Herein, besides the above-mentioned method, another method can be used, for example, a method of forming silicon as a shape of a bag and inserting the electrode unit 1 into the bag.

Figure 5A:
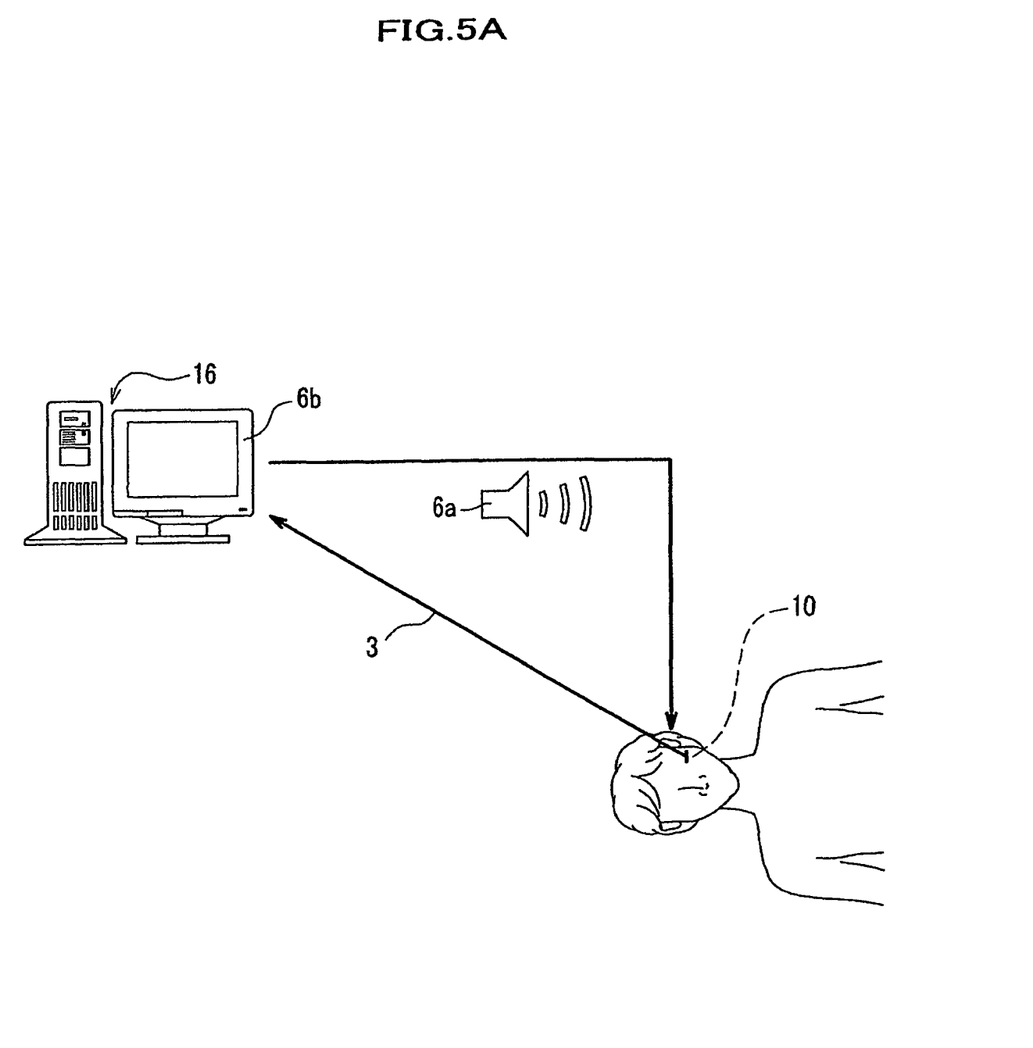
FIG. 5A is a schematic diagram showing a whole system construction of the DNAP monitoring device 16.

FIG. 5A is a schematic diagram showing a whole system construction of the DNAP monitoring device. As shown in FIG. 5A, the DNAP monitoring device 16 comprises: the DNAP monitoring electrode 10; a sound stimulator 6a for stimulating auditory sense of a patient to whom the DNAP monitoring electrode 10 is held; a display 6b for displaying potentials detected by the monitoring electrode 10; and a device which includes a control unit for controlling the sound stimulator 6a and the display 6b and an input unit.

The sound stimulator 6a is a speaker, which stimulates the auditory nerve 4 by emitting sounds toward an ear. The sound stimulator 6a is electrically connected to the control unit.

Figure 5B:
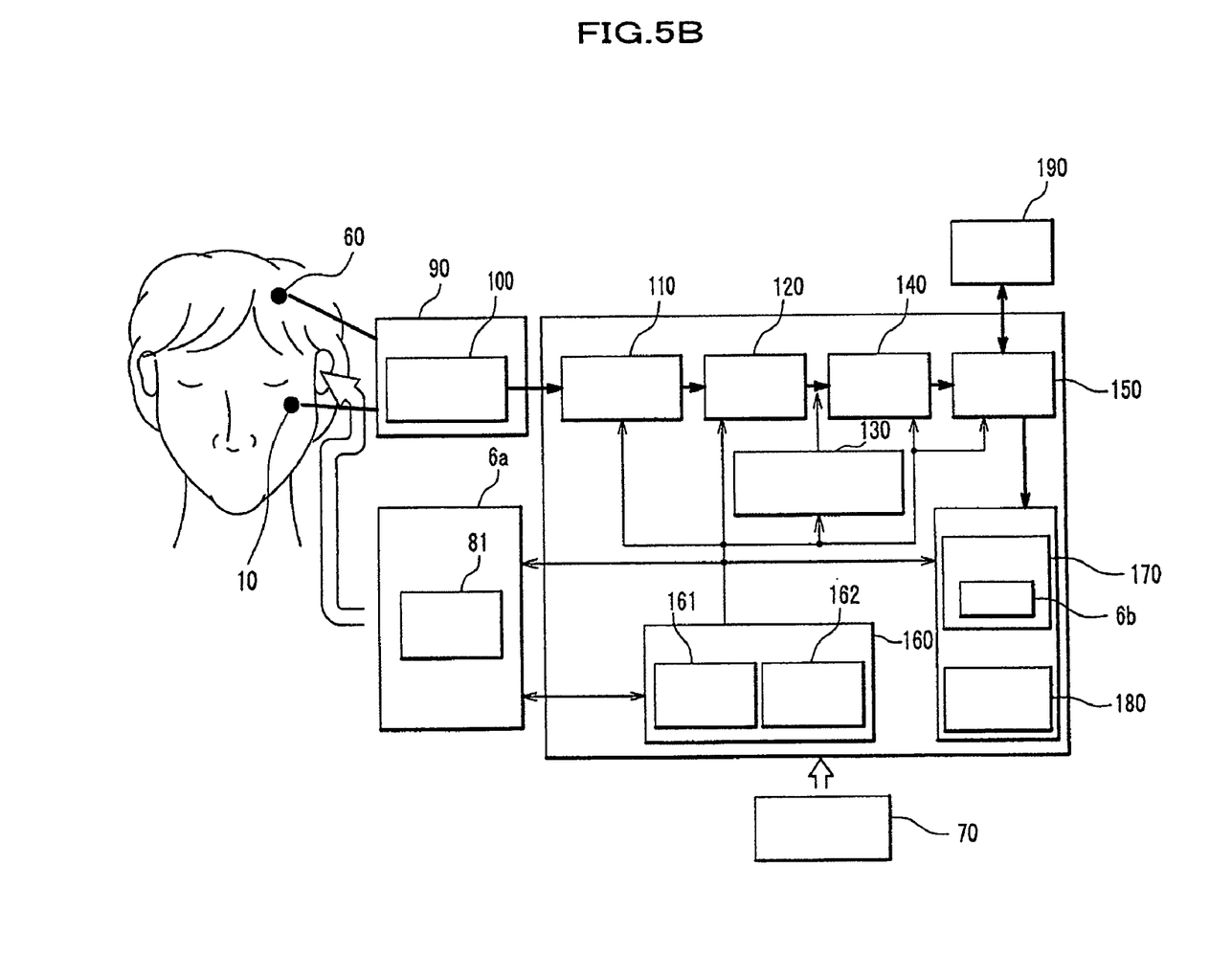
FIG. 5B is a block diagram showing a construction of the DNAP monitoring device 16.

Next, more specific configurations will be explained in reference to FIG. 5B. FIG. 5B is a block diagram showing a construction of the DNAP monitoring device 16. Main units will be explained hereinafter.

Impedance Converter

An impedance converter 100 in an input unit 90 reduces a load of an amplifier 110 through an impedance conversion. If the amplifier with sufficiently high input impedance is not used, a signal generated by a bioelectric phenomenon such as a brainwave is liable to be distorted. In this regard, in order to reduce a signal source resistor in case that the amplifier 110 is applied to a living body, it is needed to reduce the load of the amplifier 110 by using the impedance converter 100. A reference electrode 60 and the monitoring electrode 10 are electrically connected to the input unit 90. Potential differences detected between the reference electrode 60 and the monitoring electrode 10 are inputted into the input unit 90. It is preferable that the impedance conversion is performed near the electrode as close as possible.

Amplifier

An amplifier 110 in FIG. 5B is a differential amplifier. The amplifier 110 amplifies the detected potential differences by a predetermined amplification factor. Background noises in the same phase, which are detected by both reference electrode 60 and monitoring electrode 10, are deleted by the amplifier. Output of the differential amplifier extracts required frequency components through a filter circuit not shown and reduces unnecessary components such as background noises.

A/D Converter

Output of the amplifier 110 is a continuous electric signal of an amplified brainwave signal. An A/D converter 120 converts the continuous analogous electric signal to a digital signal.

Excessive Input Eliminating Device

An excessive input eliminating device 130 performs adding and averaging by an adding unit so as to reduce background noises. If there is an excessive input, the device 130 eliminates the input from adding processing data.

Adding Unit

An adding unit 140 is a circuit to perform adding and averaging processing.

Data Memory

A data memory 150 stores data generated by the excessive input eliminating device 130 and the adding unit 140.

Control Unit

A control unit 160 comprises CPU (central processing unit of a computer) 161 and a program memory 162. The control unit 160 is a device for driving the sound stimulator 6a and the display 6b based on an input signal from the input unit 90, and is electrically connected to a power supply unit 70. The control unit 160 has a function of an amplifier for amplifying weak potentials detected by the DNAP monitoring electrode 10 and driving the display 6b. By introducing a monitoring method using the novel DNAP monitoring electrode 10, a feedback system and a system that can change an operation method and strategy to the best ones corresponding to the monitoring results, can be available. Further, an operation in which an auditory function can be preserve in a high probability, which has been regarded to be very difficult, can be available.

Display Unit

The display 6b of a display unit 170 is a liquid crystal screen as shown in FIG. 5A. As shown in FIG. 8C, on a display screen, a vertical axis represents a potential and a horizontal axis represents a time. A switch (input means) is provided for turning on and turning off, and a selection of amplitude is possible. The display 6b is electrically connected to the control unit 160. Hereby, it is possible to display an input waveform, condition configuration, and a processing state, as a display of a digital computer.

Recording Unit

A recording unit 180 is a universal printer, preferably, an inkjet printer and a laser printer.

External Storage

An external storage 190 stores the data stored in the data memory 150, and data used for the monitoring device 16 and monitoring procedures. The external storage 190 exchanges the storage data with the data memory 150.

Sound Stimulator

A sound stimulator 6a generates a sound stimulus 81.

As mentioned above, detailed and specific examples and configurations have been explained according to the present embodiment. However, the present invention is not limited to the above-mentioned embodiment. A modification and alteration thereof are possible in the same technological idea. For example, in the present embodiment, with respect to a size of the exposed face 1a, the width W2 is 1.5 mm, the length L2 is 3.0 mm, and the shape is oval. However, the size is not limited to this as mentioned above. It is possible to set the size in a range, for example, the width W2 in a rage of 0.5 mm to 3.0 mm, the length L2 in a range of 0.5 mm to 5.5 mm. Further, the shape is not limited to oval. It is possible to make the shape elliptic with a tapered wedge and trapezoid with round corners to more suitably fit to a size of the dorsal cochlear nucleus.

Further, with respect to a size of the covering unit 2, the width W1 is 3.0 mm, and the length L1 is 5.5 mm. The length L1 may be 10 mm. In this case, L of the electrode unit 1 may be 8 mm, and L2 of the exposed face 1a may be 6 mm.

Further, shapes of the electrode unit 1 and the covering unit 2 are not limited to oval. Other shapes such as circle, elliptic, trapezoid, rectangular, and triangle, may be used. The material of the electrode is described as platinum and the material of the covering unit is described as silicon, hereinbefore. However, the materials are not limited to the above mentioned materials and other materials can be used.

We claim:

1. A monitoring electrode for monitoring dorsal cochlear nucleus action potentials, which is to be used in a brain surgery operation, being configured to be placed between a peduncle and a floor of a fourth ventricle and to be held onto the dorsal cochlear nucleus located between the peduncle and the floor of the fourth ventricle to monitor the dorsal cochlear action potentials, the monitoring electrode comprising:
    an electrode unit configured to detect the dorsal cochlear nucleus action potentials, wherein the electrode unit comprises a front face part of which is an exposed face exposed to detect the action potentials, and
    a covering unit comprising a front cover and a back cover made of a biocompatible resin and configured to partially cover both front and rear faces of the electrode unit with the exposed face uncovered by an opening part and protrude from a periphery of the electrode unit, the covering unit including:
        a round portion formed on the electrode unit and configured to facilitate an insertion of the electrode unit through a foramen of Luschka between the peduncle and the floor of the fourth ventricle, and
        an outer diameter shape of the covering unit having a width in a range of 3.0 mm to 3.5 mm and a length in a range of 5.5 mm to 10 mm and configured to fit in between the peduncle and the floor of the fourth ventricle,
    wherein the monitoring electrode comprises only a single electrode.

2. The monitoring electrode for monitoring the dorsal cochlear nucleus action potentials according to claim 1, wherein the exposed face has a width in a range of 0.5 mm to 3.0 mm and a length in a range of 0.5 m to 5.5 mm and is configured to fit to a region of the dorsal cochlear nucleus.

3. The monitoring electrode for monitoring the dorsal cochlear nucleus action potentials according to claim 1, wherein the outer diameter shape of the covering unit is formed in an oval shape and the exposed face has also an oval shape.

4. The monitoring electrode for monitoring the dorsal cochlear nucleus action potentials according to claim 1, wherein the biocompatible resin is made of silicon.

5. A monitoring device for monitoring dorsal cochlear nucleus action potentials comprising:
    the monitoring electrode configured to monitor the dorsal cochlear nucleus action potentials according to claim 1;
    a sound stimulator configured to stimulate an auditory sense of a patient to whom the monitoring electrode for monitoring the dorsal cochlear nucleus action potentials is held;
    a display configured to display the action potentials detected by the monitoring electrode for monitoring the dorsal cochlear nucleus action potentials;
    an amplifier configured to exclude noises mixing in the same phase, and
    an A/D converter configured to convert an analogue signal to a digital signal.

* * * * *